(12) United States Patent
Jackson et al.

(10) Patent No.: US 10,941,444 B2
(45) Date of Patent: Mar. 9, 2021

(54) FUNCTIONAL LIGANDS TO LIPOARABINOMANNAN

(71) Applicant: Base Pair Biotechnologies, Inc., Pearland, TX (US)

(72) Inventors: George W. Jackson, Pearland, TX (US); Robert Batchelor, Pearland, TX (US); Rafal Drabek, Houston, TX (US); Caitlin Bruns, Webster, TX (US)

(73) Assignee: Base Pair Biotechnologies, Inc., Pearland, TX (US)

( * ) Notice: Subject to any disclaimer, the term of this patent is extended or adjusted under 35 U.S.C. 154(b) by 0 days.

(21) Appl. No.: 16/262,777

(22) Filed: Jan. 30, 2019

(65) Prior Publication Data

US 2019/0249245 A1 Aug. 15, 2019

Related U.S. Application Data

(63) Continuation of application No. 15/893,532, filed on Feb. 9, 2018, now Pat. No. 10,415,041.

(60) Provisional application No. 62/624,068, filed on Jan. 30, 2018, provisional application No. 62/666,263, filed on May 3, 2018, provisional application No. 62/460,786, filed on Feb. 18, 2017, provisional application No. 62/456,847, filed on Feb. 9, 2017.

(51) Int. Cl.
| | | |
|---|---|---|
| *C12N 15/11* | (2006.01) |
| *C12Q 1/6874* | (2018.01) |
| *C12N 15/115* | (2010.01) |
| *C12N 15/10* | (2006.01) |
| *C12Q 1/6806* | (2018.01) |
| *C12Q 1/6837* | (2018.01) |
| *C12Q 1/6848* | (2018.01) |
| *C12Q 1/6876* | (2018.01) |
| *C40B 30/04* | (2006.01) |

(52) U.S. Cl.
CPC ........ *C12Q 1/6874* (2013.01); *C12N 15/1048* (2013.01); *C12N 15/115* (2013.01); *C12Q 1/6806* (2013.01); *C12Q 1/6837* (2013.01); *C12Q 1/6848* (2013.01); *C12Q 1/6876* (2013.01); *C40B 30/04* (2013.01); *C12N 2310/16* (2013.01); *C12N 2330/31* (2013.01)

(58) Field of Classification Search
CPC .................................................. C12N 15/115
See application file for complete search history.

(56) References Cited

U.S. PATENT DOCUMENTS

2007/0027309 A1* 2/2007 Weinstock ........... C12Q 1/6895
536/23.7

* cited by examiner

*Primary Examiner* — Ekaterina Poliakova-Georgantas
(74) *Attorney, Agent, or Firm* — Equip LG; Christopher Quan

(57) ABSTRACT

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules, such as lipoarabinomannan (LAM).

10 Claims, 5 Drawing Sheets
Specification includes a Sequence Listing.

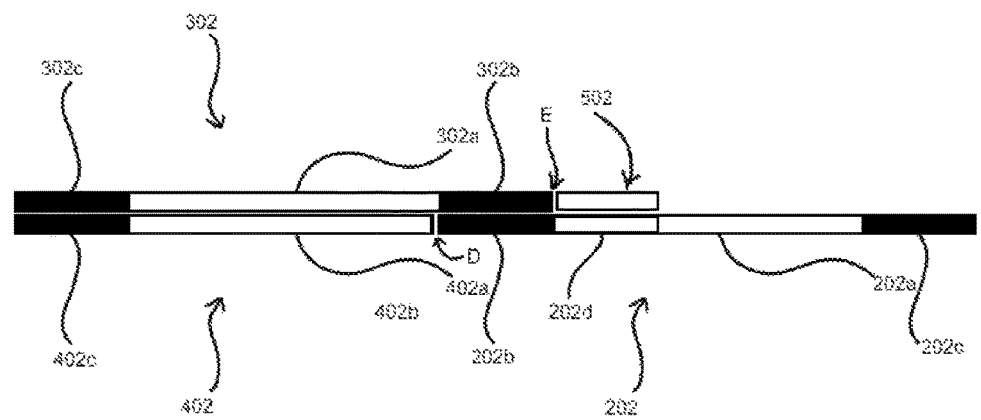
Fig.6c.
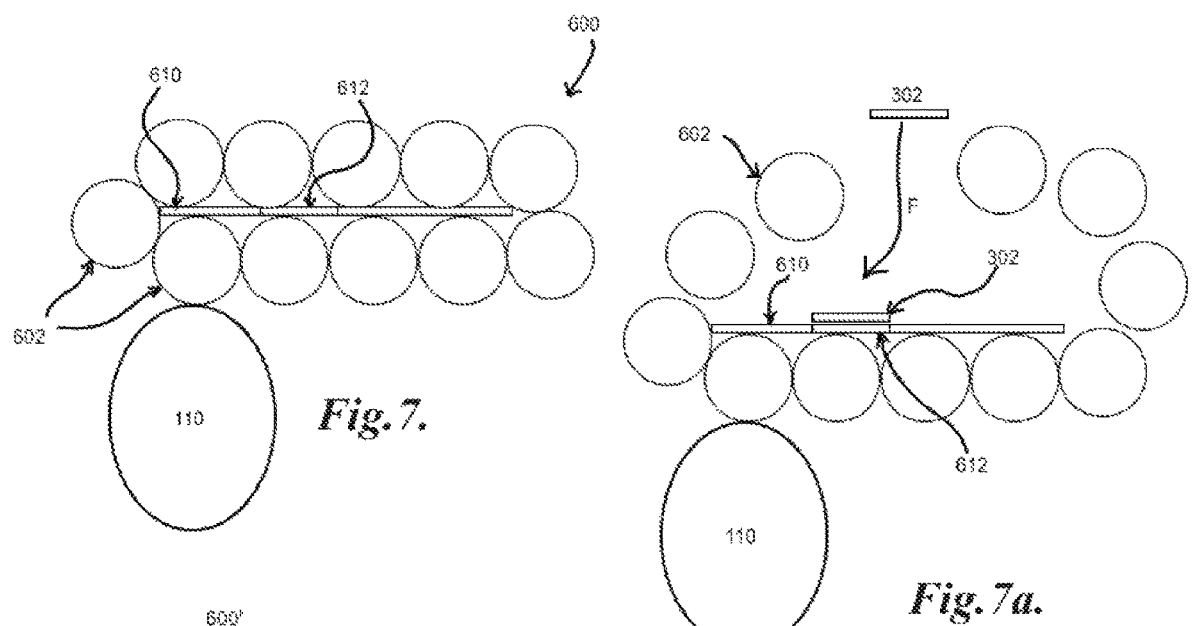
Fig.7.
Fig.7a.
Fig.7b.
Fig.7c.

SEQUENCE LISTING

```
<160> NUMBER OF SEQ ID NOS: 71

<210> SEQ ID NO 1
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 1
aaggcgtcga gaaatccagt tacactagga ca                                    32

<210> SEQ ID NO 2
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 2
aatagcagtg agaacttgac cgtcaacaca ta                                    32

<210> SEQ ID NO 3
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 3
aagttgagaa atccccacca tactaaggga aa                                    32

<210> SEQ ID NO 4
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 4
aagttgagaa cttttaagaa aacagtcaca aa                                    32

<210> SEQ ID NO 5
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 5
aatgcagtga gaactttaaa accgtattaa ca                                    32

<210> SEQ ID NO 6
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 6
aattgagaac gctatgaaaa tagcacagtg cc                                  32

<210> SEQ ID NO 7
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 7
aattgagaaa tcccaacggt ccataaaagg ga                                  32

<210> SEQ ID NO 8
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 8
aattgagaac cctgataagg aaacagagca ct                                  32

<210> SEQ ID NO 9
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 9
aattgagaac gctttgatct cagacttagc tt                                  32

<210> SEQ ID NO 10
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 10
aattgagaac ttgaattaaa agtacatctc ac                                  32

<210> SEQ ID NO 11
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 11
aattgagaac tgtaagacca tgtaaactag ca                                  32

<210> SEQ ID NO 12
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 12
aattgagaac tgttgttagt caacccaagg at                                 32

<210> SEQ ID NO 13
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 13
aattgagaat gacgccaggg tgttacacag aa                                 32

<210> SEQ ID NO 14
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 14
aattgagaac tttccacaaa tgaaccagaa aa                                 32

<210> SEQ ID NO 15
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 15
aattgagaac tttgaaatca aatcagccac ta                                 32

<210> SEQ ID NO 16
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 16
aattgagaac tttttaccga tacatcataa ac                                 32

<210> SEQ ID NO 17
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 17
aattgaggac tctataatga tagcatatgc at                                 32

<210> SEQ ID NO 18
<211> LENGTH: 32
<212> TYPE: DNA
<213> ORGANISM: Artificial Sequence
```

```
<220> FEATURE:
<223> OTHER INFORMATION: Non-naturally occuring artificial aptamer
      sequence binding to Lipoarabinomannan.

<400> SEQUENCE: 18
aattgaggac tctcacaatg agctaaggta ca                                    32

<210> SEQ ID NO 19
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 19
aaatcctaga atccatggag aactcttaaa ga                                    32

<210> SEQ ID NO 20
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 20
aagcagcagt gagaacgttt tactagaaaa cc                                    32

<210> SEQ ID NO 21
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 21
agggcagtga gaacgaaaat tttttatgcg ca                                    32

<210> SEQ ID NO 22
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 22
acaattgaga acgcttatcc atccaactaa ca                                    32

<210> SEQ ID NO 23
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 23
acattgagaa ctgtttttaa gaaccccgaa ga                                    32

<210> SEQ ID NO 24
<211> LENGTH: 32
<212> TYPE: DNA
<213> ORGANISM: Artificial Sequence
<220> FEATURE:
```

<223> OTHER INFORMATION: Non-naturally occuring artificial aptamer
      sequence binding to Lipoarabinomannan.

<400> SEQUENCE: 24
acatgaagag gcgccaggac tcaggctgct ta                                    32

<210> SEQ ID NO 25
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 25
acggcagtga gaacgcaaaa ttcaaatatt aa                                    32

<210> SEQ ID NO 26
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 26
agatagcgtt gagaacgatg aacaatcagc tt                                    32

<210> SEQ ID NO 27
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 27
cacttatggc tcaagaggcg cggaagccgg ac                                    32

<210> SEQ ID NO 28
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 28
cagcaaacag agagccgcca gttgggaacg ta                                    32

<210> SEQ ID NO 29
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 29
caggctccgc tgcattgagg cgcgcaagat aa                                    32

<210> SEQ ID NO 30
<211> LENGTH: 32
<212> TYPE: DNA
<213> ORGANISM: Artificial Sequence
<220> FEATURE:
<223> OTHER INFORMATION: Non-naturally occuring artificial aptamer sequence binding to Lipoarabinomannan.

<400> SEQUENCE: 30
agttgagaac gctccctgga gtcaaaagat aa             32

<210> SEQ ID NO 31
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 31
agttgagaac cctgtacttt aaacctctcc aa             32

<210> SEQ ID NO 32
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 32
agttgagaac tttaagaaag gaatggctaa ca             32

<210> SEQ ID NO 33
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 33
agttgagaac gtaagataat attacacgct aa             32

<210> SEQ ID NO 34
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 34
agttgagagc gtagttagtt ctgtaaccga gg             32

<210> SEQ ID NO 35
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 35
atcgcagtga gaacgtttga caaaacaaga aa             32

<210> SEQ ID NO 36
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 36
attgagaacg tcaaaattta cagttgatga ca                        32

<210> SEQ ID NO 37
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 37
cagttgagaa cgtttacaaa acataaaatc ac                        32

<210> SEQ ID NO 38
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 38
cagttgagaa cttattcaca catagccagc gc                        32

<210> SEQ ID NO 39
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 39
ccacaagggc tggaggcgct gagagagtag ta                        32

<210> SEQ ID NO 40
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 40
ccgcgtagcg gcagtgagga ctctcaatca gt                        32

<210> SEQ ID NO 41
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 41
cgttgttcaa ccagttggga actctaccct tt                        32

<210> SEQ ID NO 42
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

```
<400> SEQUENCE: 42
ctagcagtga gaatgacttt gaaaaatccg cc                                      32

<210> SEQ ID NO 43
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 43
ctagggcagt gaggactcat tttaagatgc ag                                      32

<210> SEQ ID NO 44
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 44
ctcgcgttga gaacgtttaa aaaactatat ca                                      32

<210> SEQ ID NO 45
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 45
ctgtagggct tcagaggcgc cgaacgccag ca                                      32

<210> SEQ ID NO 46
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 46
cttctgcatc tatcggcgtc aagctgactc gc                                      32

<210> SEQ ID NO 47
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 47
gaaaagccta gagattgagc gcagagaatg ac                                      32

<210> SEQ ID NO 48
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 48
```
gaagcaacga taccgcgcca cgacctcaag ca                                32

<210> SEQ ID NO 49
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 49
gaatagtgat agcaaagagc atcgggaacg aa                                32

<210> SEQ ID NO 50
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 50
gagttgagaa ctttcagtca ccgataaaca ta                                32

<210> SEQ ID NO 51
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 51
gattatcacg ttgaaaggcg ctacaataga aa                                32

<210> SEQ ID NO 52
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 52
gattcagagc agtgagaacg ccaaatttgt tc                                32

<210> SEQ ID NO 53
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 53
gtattgcagc gagaacgtcg aaatatatga ca                                32

<210> SEQ ID NO 54
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 54
gtcagcacac caggcgtctg aacggtcaag gc    32

<210> SEQ ID NO 55
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 55
gtcggccact taagccaagc agggagaatg ca    32

<210> SEQ ID NO 56
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 56
ggatacgcac gacgcgacgc aggccaacag ga    32

<210> SEQ ID NO 57
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 57
ggcacggtcg cagcgagaat ctccctaaaa ag    32

<210> SEQ ID NO 58
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 58
taggggcagt gagaacgcaa aaagaatag ac    32

<210> SEQ ID NO 59
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 59
taggggcagt gagaacgcaa ataggaatag ac    32

<210> SEQ ID NO 60
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 60
tagttgagaa cttgataaca ctgaacctaa aa    32

<210> SEQ ID NO 61
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 61
ttgcagggag aacttctata cttagactct gc                                    32

<210> SEQ ID NO 62
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 62
tcctgcagtg ggaacccgt aatgttctta ca                                     32

<210> SEQ ID NO 63
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 63
tcctgcattg agaacctta gtgagttatg aa                                     32

<210> SEQ ID NO 64
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 64
tgtggtgttg agaacgattc aaaatctgcc cc                                    32

<210> SEQ ID NO 65
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 65
ttgtcagaga gaacttcatt agacactaac cc                                    32

<210> SEQ ID NO 66
<211> LENGTH: 32
<212> TYPE: DNA
<213> ORGANISM: Artificial Sequence
<220> FEATURE:

```
<223> OTHER INFORMATION: Non-naturally occuring artificial aptamer
      sequence binding to Lipoarabinomannan.

<400> SEQUENCE: 66
tttatgcgtt gacggcgata tcgttaagag gc                                    32

<210> SEQ ID NO 67
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 67
tttgagaact ttaccacgga acacgaaata ac                                    32

<210> SEQ ID NO 68
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 68
tttgagaact ttttacaaac gggcgggata ac                                    32

<210> SEQ ID NO 69
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to Lipoarabinomannan.

<400> SEQUENCE: 69
tttgagaatg gagaggttcg tcttaagtag tt                                    32

<210> SEQ ID NO 70
<211> LENGTH: 19
<212> TYPE: DNA
<213> ORGANISM: Artificial Sequence
<220> FEATURE:
<223> OTHER INFORMATION: Artificial, non-naturally occuring 5' primer
      sequenc

<400> SEQUENCE: 70
gcgccggagt tctcaatgc                                                   19

<210> SEQ ID NO 71
<211> LENGTH: 19
<212> TYPE: DNA
<213> ORGANISM: Artificial Sequence
<220> FEATURE:
<223> OTHER INFORMATION: Artificial, non-naturally occuring 3' primer
      sequence

<400> SEQUENCE: 71
gcatgccggt cggtctact                                                   19
```

FUNCTIONAL LIGANDS TO LIPOARABINOMANNAN

CROSS-REFERENCE TO RELATED APPLICATIONS

This application claims the benefit and priority of U.S. provisional patent application Ser. No. 62/624,068, filed Jan. 30, 2018, entitled "FUNCTIONAL LIGANDS TO LIPOARABINOMANNAN", the contents of which is hereby incorporated by reference in its entirety.

FIELD OF THE INVENTION

This invention relates to functional ligands to target molecules, particularly to functional nucleic acids and modifications thereof, more particularly to functional ligands with binding affinity to target molecules such as lipoarabinommanan (LAM).

SEQUENCE LISTING

Deoxyribonucleic acid (DNA) sequences, which are disclosed in the ASCII text file entitled "PLAMUS00_ST25.txt", created on Jan. 30, 2018 and of 18.2 KB in size, which is incorporated by reference in its entirety, herein are intended to include other aptamers incorporating modifications, truncations (e.g. trivial truncations, such as 1-5 nucleotides removed at an end, which consist essentially of the same sequence and retains binding to the target molecule), incorporations into larger molecules or complexes (e.g. the aptamer sequence within a longer nucleic acid strand), and/or other aptamers having substantial structural or sequence homology, for example, greater than 75-90% sequence homology within a similar length of nucleic acid (e.g. similar to within 5-10 nucleotides in length with significant sequence homology within that length, such as greater than 75-90%), as well as RNA and/or other non-DNA/RNA aptamers. The disclosed aptamers may also bind to homologous proteins or molecules from organisms other than the organisms listed herein, to recombinant or non-recombinant versions of the proteins or molecules, to modified versions of the proteins or molecules, to proteins or molecules from sources other than the source listed herein. The aptamers are artificial, non-naturally occurring sequences designed and/or selected for specific and/or high affinity binding to a target molecule, such as, without limitation, SEQ ID Nos. 1-69 may bind to lipoarabinomanan (LAM). Non-naturally occurring sequences of aptamers, may also not be present in naturally occurring systems or situations, such as by, for example, not being already present or having a pre-existing function in a naturally occurring setting. The indication of the species and source of the target proteins or molecules is given for reference only and is not intended to be limiting. SEQ ID No. 70 may generally be utilized as a leading or priming sequence appended to the 5'-end of any of the aptamer sequences, and SEQ ID No. 71 may generally be utilized as a trailing or priming sequence appended to the 3'-end of any of the aptamer sequences, or vice versa or any combination thereof.

BACKGROUND OF THE INVENTION

Aptamers, which are nucleic acid ligands capable of binding to molecular targets, have recently attracted increased attention for their potential application in many areas of biology and biotechnology. They may be used as sensors, therapeutic tools, to regulate cellular processes, as well as to guide drugs to their specific cellular target(s). Contrary to the actual genetic material, their specificity and characteristics are not directly determined by their primary sequence, but instead by their secondary and/or tertiary structure. Aptamers have been recently investigated as immobilized capture elements in a microarray format. Others have recently selected aptamers against whole cells and complex biological mixtures. Aptamers are typically characterized by binding to their target molecules via non-Watson-Crick (i.e. non-hybridization) mechanisms, such as by intermolecular forces resulting from the secondary or tertiary structure of the aptamer. This is especially true of non-nucleic acid target molecules where Watson-Crick mechanisms typically do not apply.

Aptamers are commonly identified by an in vitro method of selection sometimes referred to as Systematic Evolution of Ligands by EXponential enrichment or "SELEX". SELEX typically begins with a very large pool of randomized polynucleotides which is generally narrowed to one aptamer ligand per molecular target. Once multiple rounds (typically 10-15) of SELEX are completed, the nucleic acid sequences are identified by conventional cloning and sequencing. Aptamers have most famously been developed as ligands to important proteins, rivaling antibodies in both affinity and specificity, and the first aptamer-based therapeutics are now emerging. More recently, however, aptamers have been also developed to bind small organic molecules and cellular toxins, viruses, and even targets as small as heavy metal ions. After identification of an aptamer sequence from sequencing after SELEX, the aptamer is typically manufactured afterwards in manners utilized with any other oligonucleotide, such as by standard synthesis methods, such as standard commercial nucleic acid synthesis (e.g. oligonucleotide synthesis by phosphoramidite method, etc.), or the sequence may be utilized with biological synthesis methods, such polymerase chain reaction (PCR) or the like.

Lipoarabinomannan (LAM) is a lipoglycan and major virulence factor in the bacteria genus Mycobacterium, such as *Mycobacterium tuberculosis,* the bacteria responsible for tuberculosis. In addition to serving as a major cell wall component, it is thought to serve as a modulin with immunoregulatory and anti-inflammatory effects. This allows the bacterium maintain survival in the human reservoir by undermining host resistance and acquired immune responses. These mechanisms include the inhibition of T-cell proliferation and of macrophage microbicidal activity via diminished IFN-γ response. Additional functions are thought to include the neutralization of cytotoxic oxygen free radicals produced by macrophages, inhibition of protein kinase C, and induction of early response genes.

SUMMARY OF THE INVENTION

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules, more particularly to functional ligands with binding affinity to molecules such as lipoarabinomannan (LAM).

In general, a method for generating functional biomolecules includes obtaining a library, such as a diverse or randomized library, for example, of biomolecules. Biomolecules may generally include nucleic acids, particularly single-stranded nucleic acids, peptides, other biopolymers and/or combinations or modifications thereof. A library of biomolecules may include nucleic acid sequences, such as ribonucleic acid (RNA), deoxyribonucleic acid (DNA), artificially modified nucleic acids, and/or combinations thereof. The method for generating functional biomolecules further includes contacting the library of biomolecules with more than one target, such as, for example, a molecular target, material and/or substance. In general, the members of the library that do not bind with some affinity to the more than one target may be washed or otherwise partitioned from the remainder of the library, which may have a given level of binding affinity to the more than one target. The process may be repeated to partition the strongest binding members of the library. Amplification of the biomolecules may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity, such biomolecules generally referred to as aptamers or ligands.

In one exemplary aspect of the invention, generation of functional biomolecules may be performed against more than one or multiple targets simultaneously within a single system, such as the generation of functional nucleic acid ligands within a single reaction volume. In general, more than one or a plurality of targets may be disposed within in a single reaction volume, and a library of biomolecules, such as a nucleic acid library, may be applied to the reaction volume. The members of the library that do not bind to any of the plurality of targets under given conditions may then be partitioned, such as by washing. One or more rounds of binding and partitioning of the members of the library may be performed, such as, for example, to obtain a remainder of members of the library with a given affinity for their targets. The remaining members that bind to the plurality of targets of the library may then be marked and/or tagged, such as to identify the particular target or targets to which the member(s) of the library binds. The binding members of the library may then be isolated and, by virtue of the marking or tagging, be matched to a particular target or targets. This is desirable as high capacity, multiplexed identification procedures may save time, expense, and physical space for the process over single target identification processes. The present method may also be desirable as it may be utilized to identify and/or eliminate biomolecules that bind or have a tendency to bind to multiple targets.

In an exemplary embodiment, a plurality of target molecules are affixed to a substrate within a single reaction volume, such as, for example, by attaching the targets to a substrate of an array. It may generally be appreciated that a single reaction volume may refer to or include multiple reaction sub-volumes, such as, for example, discrete or semi-discrete fluid droplets. In general, the targets may be disposed with multiple copies of each target in clusters or "spots" such that a given array may have an ordered deposition of targets on the substrate, with each target identifiable by the location of a particular spot on the substrate. A library of nucleic acids may then be contacted or applied to the array and the non-binding members of the library may be partitioned or washed off the array. The binding and washing steps may be repeated and may also utilize an amplification step to generate additional copies of any remaining binding members of the library. The array may then be marked or tagged with a plurality of identifiers, such as, for example, a plurality of oligonucleotides which may universally bind through Watson-Crick interactions to the members of the library of nucleic acids. The marking or tagging may be, for example, accomplished by manually applying identifiers, such as by pipetting or the like, utilizing microcontact pins, applying membranes/films with identifiers, printing, for example, inkjet printing, and/or other similar tagging methods, of identifier containing solutions to the array. The identifiers may further include a unique or semi-unique sequence which may be utilized to correspond to the spots and thus the targets of the array. For example, a unique or semi-unique identifier sequence may be utilized that identifies each spatial location on an array, such as each particular target spot. The identifier may then be associated with and/or attached to the nucleic acid members bound to a particular spot. Thus, the nucleic acids, for example, bound to a particular target spot may be identified by the sequence of the associated identifier. In some embodiments, the identifiers may further be primers and may be utilized with a nucleic acid amplification reaction on the array to generate additional copies of the bound nucleic acids. The unique or semi-unique identifier sequence may also be incorporated into the members of the library amplified. This may be desirable for associating a given member with a target or targets while preserving the particular sequence of the member as the locational identifying sequence is appended to the sequence of the library member. This may be particularly desirable for resolving multiple binders to a single target or members of the library that bind to multiple targets.

In general, the starting library of biomolecules, such as nucleic acids, may be the product of at least one round of a previous SELEX protocol. For example, at least one round of SELEX may be performed with a library of biomolecules against multiple targets, such as, for example, in a solution. The targets in the solution may be substantially identical to the targets disposed on an array. This may be desirable as multiple rounds of selection may be performed with a library prior to applying the remaining members to an array for marking/tagging. Complex target arrays may generally be more expensive and/or difficult to make or utilize than solutions of target molecules, so performing only the final binding and marking/tagging procedure on the array may be desirable.

In other embodiments, identifiers may be predisposed on the array substrate in substantial proximity to the spots such that they may bind to, for example, nucleic acids bound to the target spots. The identifiers may, for example, be covalently attached to the substrate. In some embodiments, the attachments may be controllably breakable or cleavable such that the identifiers may be released from the substrate such that they may, for example, more easily bind to the bound nucleic acids on the spots.

In further embodiments, identifiers may be synthesized in situ on the array, such as by light directed in situ nucleic acid synthesis. Appropriately sequenced identifiers may then be synthesized in proximity to particular spots such that the newly synthesized identifiers may bind to the nucleic acids bound to the target spot.

In still other embodiments, identifiers may be disposed and/or synthesized on a separate substrate, such as a membrane, in a spatial disposition that substantially matches the spatial disposition of spots on the array, i.e. the identifiers may be arranged such that they may be readily superimposed onto the target spots on the array. The identifier substrate may then be contacted with the array with locational matching of the spots with identifiers. The identifiers may then bind to the nucleic acids bound to the target spots. Any appropriate method of facilitating binding may be utilized, such as, for example, actions to drive migration of the identifiers to the array, such as capillary action, electrophoresis, pressure, gravitational settling, and/or any other appropriate method or combination thereof. The separate substrate may also be soluble, erodible, substantially permeable to the identifiers, and/or otherwise adapted for facilitating migration of the identifiers to the array.

In yet still other embodiments, the array substrate may be physically divided and/or partitioned for separate collection of the, for example, nucleic acids bound to the spots. The spots may, for example, also be controllably removable from the substrate such that they may be individually recovered and sorted.

In still yet other embodiments, identifiers may be disposed and/or synthesized on a separate substrate, such as a membrane, in a spatial disposition that substantially matches the spatial disposition of spots on the array, i.e. the identifiers may be arranged such that may be readily superimposed onto the target spots on the array. The separate substrate may be kept separately while the array substrate maybe physically divided and/or partitioned for separate collection of the nucleic acids bound to the spots. In this manner, the location of the different nucleic acids maybe maintained even when the array substrate is no longer intact, if the locations are of value. The identifiers may also be selectively applied to particular locations on the array and/or applied in a particular order or in groups.

In some embodiments, identifiers may only be applied to spots with bound nucleic acids. The spots with bound nucleic acids may be detected, for example, by detecting the presence of nucleic acids, such as by applying nucleic acid binding dyes, such as SYBR dyes, ethidium bromide and/or other appropriate dyes. The members of the nucleic acid library may also include detectable portions, such as, for example, fluorescent moieties, radioactive tags and/or other appropriate detectable portions.

In some embodiments, the identifiers may be applied to the bound nucleic acids together with other materials, such as for example, components of a nucleic acid amplification reaction, a nucleic acid ligation reaction, photo-linking reagents, and/or any other appropriate material, such as those materials that may facilitate attachment or association of the identifiers to the bound nucleic acids.

In yet another embodiment, identifiers may be ligated to the, for example, bound nucleic acids. For example, a nucleic acid ligase may be utilized to covalently link an identifier sequence to the bound nucleic acid. Further nucleic acid fragments may be utilized to facilitate ligase action, such as appropriate complementary fragments that may aid the formation of a substantially double-stranded nucleic acid complex compatible with a ligase. For another example, photo-ligation may be used to attach the identifiers to the, for example, bound nucleic acids. Photo-ligation may be especially useful when certain substrates are used. For example, macro-porous substrates.

In general, methods may be applied that may facilitate binding or other interactions between the identifiers and the, for example, nucleic acids bound to the spots. For example, the temperature may be increased to dissociate the nucleic acids from the spots. The temperature may subsequently be lowered such that, for example, base pairing may occur between the nucleic acids and the identifiers. Further in general, it may be desirable to apply the identifiers in a manner that physically separates and/or isolates the individual target spots such that cross-marking due to identifier diffusion/migration may be minimized. For example, the identifiers may be applied in individual fluid droplets such that there is no continuous fluid contact between individual identifier containing fluids. For further example, the substrate of the array may be absorbent and/or porous such that the identifiers may be absorbed into the substrate material. The substrate material may also block lateral diffusion while allowing vertical diffusion, such that identifiers may be applied and absorbed into the substrate while minimizing diffusion across the plane of the substrate, such as to other target spots.

In a further embodiment, a method for generating functional biomolecules includes obtaining a library of peptide sequences and contacting the library with a plurality of targets. In some exemplary embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind another identifier, as described above, such that a peptide bound to a target may be tagged or marked as to which target it bound.

In an exemplary embodiment, a bacteriophage (phage) may be generated that includes a peptide sequence of interest in its protein coat. The phage may further include a nucleic acid sequence that may be representative of the peptide sequence within the nucleic acid of the phage. The phage may then be contacted with a plurality of targets, as above. This may generally be referred to as phage display. Non-binding phages may be washed and/or partitioned, while binding phages may be tagged or marked with identifiers, as above. As phage nucleic acids are generally contained within the protein coat of the phage, the nucleic acid may generally be exposed for binding to the identifier. For example, the phage may be heated such that the protein coat denatures and/or disassembles such that the nucleic acid is exposed. The identifier may also be introduced into the phage, such as by electroporation, electrophoresis, and/or any other appropriate method.

Other methods of peptide selection may include, but are not limited to, mRNA display, ribosome display, and/or any other appropriate peptide display method or combination thereof.

In another aspect of the invention, methods for handling and sorting the resultant sequences of a multiplexed binding process are provided. In some embodiments, the sequences may be sorted by identifier sequences to establish which target or targets the sequence bound. The sequences may further be compared, aligned and/or otherwise processed to identify features, characteristics and/or other useful properties, relationships to each other, and/or target properties.

In a further aspect of the invention, methods for monitoring and/or controlling the diversity of the library of biomolecules may be utilized. For example, too few rounds of selection may result in a biomolecule pool with too many weak binding members while too many rounds of selection may result in only a few binding members, such as members corresponding to only a few targets rather than members corresponding to all of the targets present. In one embodiment, Cot analysis may be employed to measure and/or monitor the diversity of the library of biomolecules through multiple rounds of selection. Cot, or Concentration x time, analysis measures the annealing time of particular oligonucleotides while in solution with other nucleic acids, such as the members of the library of biomolecules. In general, the annealing time will be faster the lower the diversity of the library.

The present invention together with the above and other advantages may best be understood from the following detailed description of the embodiments of the invention illustrated in the drawings.

BRIEF DESCRIPTION OF THE FIGURES

FIGS. 6, 6a, 6b and 6c illustrate embodiments of identifiers and ligation of identifiers to a library member;

FIGS. 7 and 7a illustrate phage display for a target;

FIG. 7b illustrates an mRNA display fusion product;

FIG. 7c illustrates a ribosome display fusion product;

DETAILED DESCRIPTION OF THE INVENTION

Figure 1:
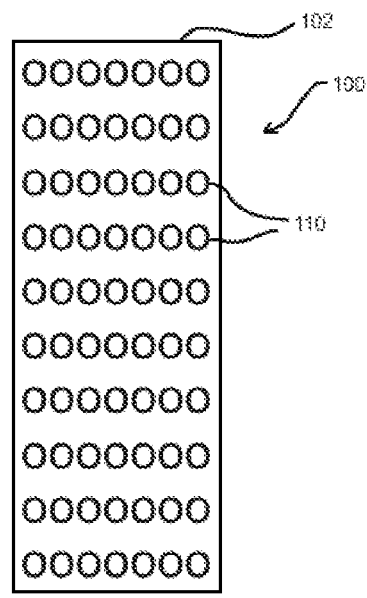
FIG. 1 illustrates an embodiment of a multiple target array.

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules, more particularly to functional ligands with binding affinity to molecules such as lipoarabinomannan (LAM). Functional ligands, particularly functional nucleic acids, of the present invention are generally artificial, non-naturally occurring sequences designed and/or selected for specific and/or high affinity binding to a target molecule, such as LAM. Non-naturally occurring sequences of functional nucleic acids, such as aptamers, may also be useful by interacting with a target molecule in a manner not present in naturally occurring systems or situations, such as by, for example, not being already present or having a pre-existing function in a naturally occurring setting.

In general, a method for generating functional biomolecules includes obtaining a library, such as a diverse or randomized library, of biomolecules. Biomolecules may generally include nucleic acids, particularly single-stranded nucleic acids, peptides, other biopolymers and/or combinations or modifications thereof. A library of biomolecules may include nucleic acid sequences, such as ribonucleic acid (RNA), deoxyribonucleic acid (DNA), artificially modified nucleic acids, and/or combinations thereof. In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, 5-Trifluoromethyl-2-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base. The method for generating functional biomolecules further includes contacting the library of biomolecules with at least one target, such as, for example, a molecular target, material and/or substance. In general, the members of the library that do not bind with some affinity to the target may be washed or otherwise partitioned from the remainder of the library, which may have a given level of binding affinity to the target. The process may be repeated to partition the strongest binding members of the library. Amplification of the biomolecules may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity. The basic SELEX protocol and aptamers are described in U.S. Pat. No. 5,270,163, entitled "Methods for identifying nucleic acid ligands," the entire contents of which are hereby incorporated by reference.

In one exemplary aspect of the invention, generation of functional biomolecules may be performed against multiple targets simultaneously within a single system, such as the generation of functional nucleic acid ligands within a single reaction volume. In general, a plurality of targets may be disposed within in a single reaction volume and a library of biomolecules, such as a nucleic acid library, may be applied to the reaction volume. The targets may be, for example, proteins, cells, small molecules, biomolecules, and/or combinations or portions thereof. The members of the library that do not bind to any of the plurality of targets under given conditions may then be partitioned, such as by washing. The remaining members of the library may then be marked and/or tagged, such as to identify the particular target or targets to which the member of the library binds. The binding members of the library may then be isolated and, by virtue of the marking or tagging, be matched to a particular target or targets. This may be desirable as high capacity, multiplexed identification procedures may save time, expense, and physical space for the process over single target identification processes. The present method may also be desirable as it may be utilized to identify and/or eliminate molecules that bind to multiple targets.

Functional ligands to LAM, without limitation and without being bound to any particular theory, may be utilized for detection, quantification, and/or other diagnostic applications, such as for detecting or quantifying levels of LAM in body fluids or tissues, or samples thereof. For example, and without being bound to any particular theory, a functional ligand such as a nucleic acid aptamer to LAM may be utilized to detect or quantify LAM for the purpose of detecting tuberculosis infection in a patient, such as with fluorescence assays. Other forms of detection may also utilize the functional ligands, such as electrochemical sensors, gold nanoparticle assays, enzyme linked aptamer sorbent assays (ELASA), pull down assays (immunoprecipitation), microplate/well assays, and/or any other appropriate form of detection.

Figure 2:
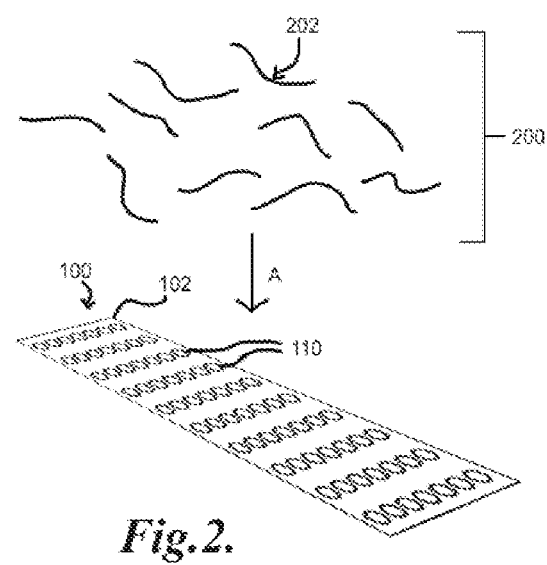
FIG. 2 illustrates the application of a library of biomolecules to a target array.
Figure 2A:
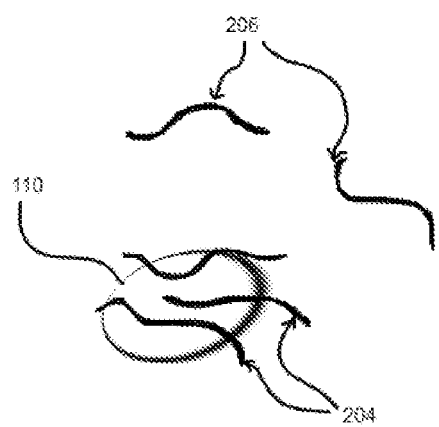
FIG. 2a illustrates the binding of members of a library of biomolecules to a target spot.
Figure 3:
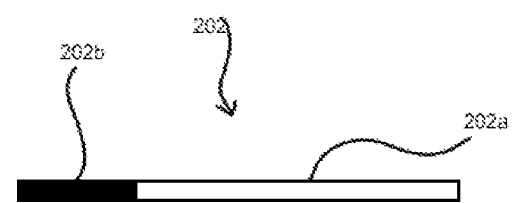
FIGS. 3 and 3a illustrate embodiments of biomolecule library members.
Figure 3A:
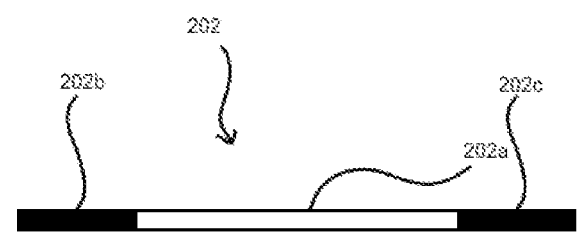
Figure 3B:
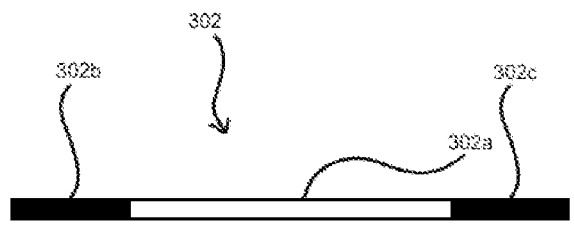
FIG. 3b illustrates an embodiment of an identifier.
Figure 4:
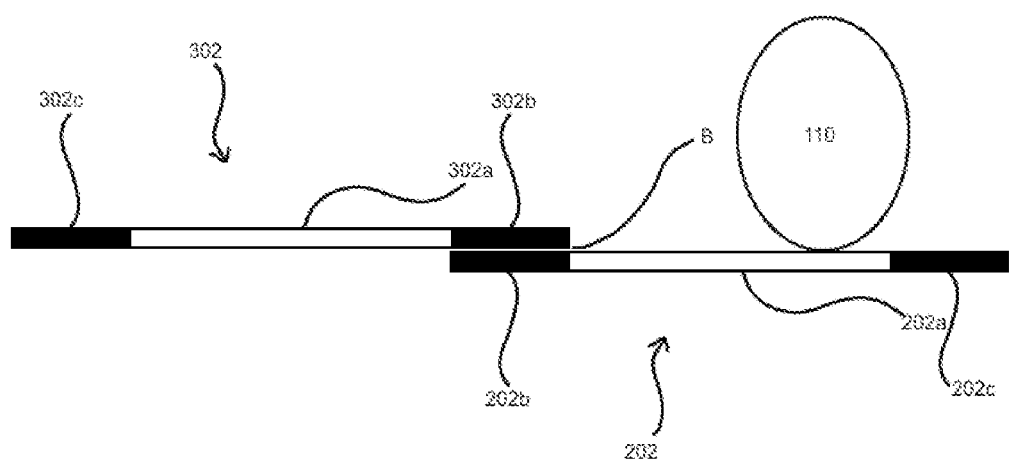
FIG. 4 illustrates the tagging of a library member bound to target with an identifier.
Figure 4A:
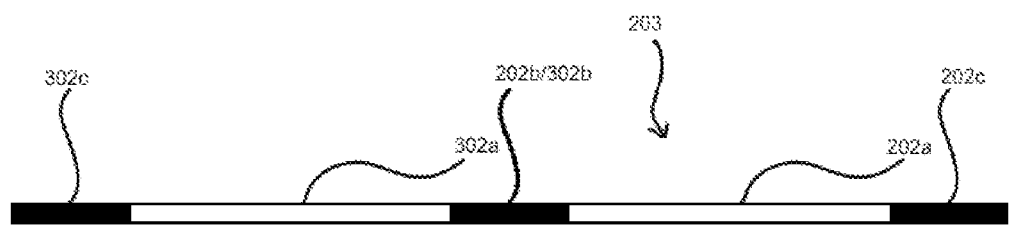
FIG. 4a illustrates a tagged library member product.

In an exemplary embodiment, a plurality of target molecules are affixed to a substrate within a single reaction volume, such as, for example, by attaching the targets to a substrate of an array. As illustrated in FIG. 1, the targets may be disposed with multiple copies of each target, such as target molecules, in clusters or "spots" 110 on the substrate 102 of an array 100 such that a given array 100 may have an ordered deposition of targets on the substrate 102, with each target identifiable by the location of a particular spot 110 on the substrate 102. Each spot 110 may be a unique target or there may be multiple spots 110 of at least one target on a given array 100. In general, high content target arrays, such as high content protein or antibody arrays or other forms of arrays recognized as high content or high density for interrogating a high number of different targets at once may be utilized. For example, human protein microarrays, such as ProtoArray® from ThermoFisher containing over 9,000 unique proteins in spotted format, may be utilized. A library 200 of, for example, nucleic acids 202 may then be applied A to array 100, as illustrated in FIG. 2. Particular members 204 of the library 200 may then bind to target spots 110, such as illustrated in FIG. 2a. The non-binding members 206 of the library 200 may be partitioned or washed off the array 100. The binding and washing steps may be repeated and may also utilize an amplification step to generate additional copies of any remaining binding members 204 of the library 200. The array 100 may then be marked or tagged with a plurality of identifiers, such as, for example, a plurality of oligonucleotides which may universally bind through Watson-Crick interactions to the members of the library of, for example, nucleic acids. In one embodiment, each member 202 of the library 200 may include a potential binding sequence 202a and at least one conserved region 202b which may bind an identifier oligonucleotide, such as illustrated in FIG. 3. A further conserved region 202c may also be included to facilitate priming for amplification or extension reactions, such as Polymerase Chain Reaction (PCR), as illustrated in FIG. 3a. In general the conserved regions 202b, 202c may flank the potential binding sequence 202a, such as to facilitate priming for amplification. An identifier 302 may then include a unique or semi-unique sequence 302a, such as illustrated in FIG. 3b, which may be utilized to correspond to the spots 110 and thus the targets of the array 100 by location of the spot 110 on the substrate 102. The identifiers 302 may further include conserved region 302b which may bind to the conserved region 202b of the library members 202 by Watson-Crick base pairing. The identifiers 302 may also include a further conserved region 302c which may facilitate priming for amplification. The identifiers 302 may be, for example, applied to the spots 110 by printing, for example, inkjet printing, using micro-contact pins, and/or otherwise applying solutions containing identifiers 302 to the substrate 102 of the array 100, such as, for example, by pipetting or the like, onto the spots 110. A library member 202 bound to a target spot 110 may then be tagged with an identifier 302 via base pairing B at regions 202b, 302b, as illustrated in FIG. 4. Thus, the nucleic acids 202 bound to a particular target spot 110 may be identified by the sequence 302a of the identifier 302. In an exemplary embodiment, nucleic acid amplification or extension, such as PCR, may be utilized to generate copies of the members 202 bound to the spots 110, incorporating the identifier sequence 302a (or more its complementary sequence) into the product 203, as illustrated in FIG. 4a. This may be desirable for associating a given member 202 with a target or targets 110 while preserving the particular sequence of the member 202. This may be particularly desirable for resolving multiple binders to a single target or members of the library that bind to multiple targets. Subsequent amplifications may utilize primers for the sequences 202c, 302c such that only the products 203 containing both the sequences 202a, 302a are amplified. It may be understood that references to nucleic acid sequences, such as above, may generally refer to either a particular sequence or the corresponding complementary nucleic acid sequence. In general, it may be desirable for single droplets and/or otherwise separated volumes of solutions containing identifiers 302 for each spot 110 on the array 100 such that the possibility of mistagging may be reduced.

In one aspect, the identifiers may be printed on all the targets. In another aspect, the identifiers may be printed only on targets with bound biomolecules.

Figure 8:
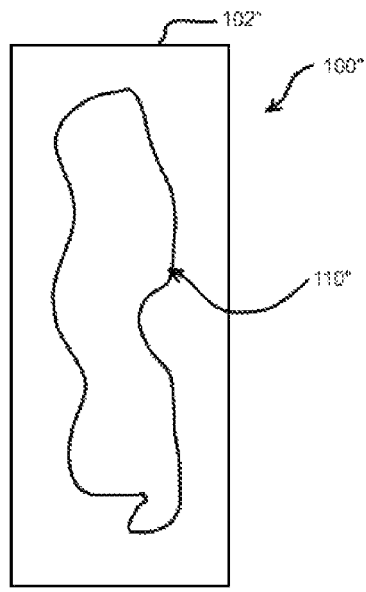
FIG. 8 illustrates an example of a histology section target.

In another embodiment, a histology section, such as the section 110" on substrate 102" of histology slide 100" in FIG. 8, may be utilized as a target set. The section 110" may be, for example, a tissue section, a cell mass, and/or any other appropriate biological sample which may generally have structurally significant features. As with the array 100, a library of biomolecules, such as nucleic acids, may be applied which may bind to specific locations on the section 110", the locations on which may, for example, represent separate targets to generate affinity binding nucleic acids. Identifiers may then be disposed on the slide 100" as described above, or as in the embodiments below, such that identifiers may be utilized to correspond to specific features of the section 110".

Figure 5:
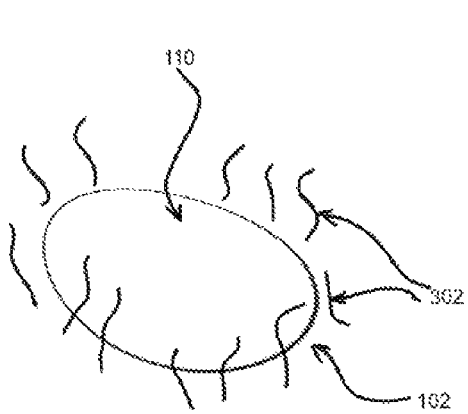
FIG. 5 illustrates a target spot with nearby identifiers on a substrate.

In other embodiments, identifiers may be predisposed on the array substrate in substantial proximity to the spots, such as illustrated with identifiers 302 disposed on substrate 102 in proximity to spot 110 in FIG. 5, such that they may bind to nucleic acids bound to the target spots. The identifiers may, for example, be covalently attached to the substrate. In some embodiments, the attachments may be controllably breakable or cleavable such that the identifiers may be released from the substrate such that they may, for example, more easily bind to the bound nucleic acids on the spots.

In further embodiments, identifiers may be synthesized in situ on the array, such as by light directed in situ nucleic acid synthesis. Appropriately sequenced identifiers may then be synthesized in proximity to particular spots such that the newly synthesized identifiers may bind to the nucleic acids bound to the spot.

Figure 5A:
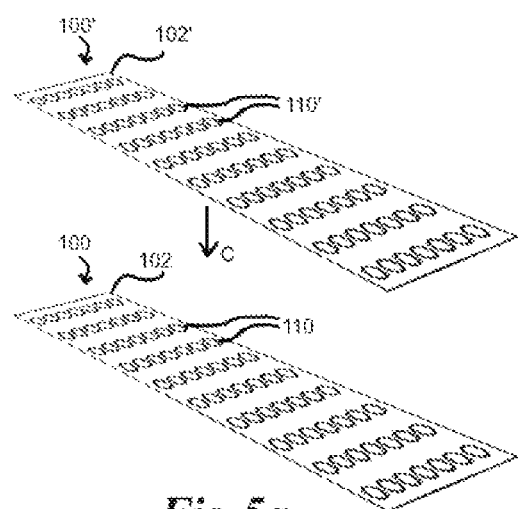
FIG. 5a illustrates the application of an identifier sheet to a target array.

In still other embodiments, identifiers may be disposed and/or synthesized on a separate substrate, such as a membrane, in a spatial disposition that matches the spatial disposition of spots on the array. FIG. 5a illustrates an example of an identifier sheet 100' with membrane 102' which may include identifier spots 110' which may substantially correspond to target spots 110 of the array 100. The identifier sheet 100' may then be contacted C with the array 100 with locational matching of the target spots 110 with identifier spots 110'. The identifiers may then bind to the nucleic acids bound to the target spots. Any appropriate method of facilitating binding may be utilized, such as, for example, actions to drive migration of the identifiers to the array, such as capillary action, electrophoresis, pressure, gravitational settling, and/or any other appropriate method or combination thereof.

In some embodiments, the membrane may be soluble and/or substantially erodible. For example, the membrane may include a film forming and/or soluble material. Identifiers and/or other materials, such as components of a nucleic acid amplification or ligation reaction, may be included such that a film is formed containing the desired materials. The membrane may then be applied to the substrate and a suitable solvent, such as water or ethanol, may be utilized to dissolve and/or erode the film, which may then release the included materials, such as the identifiers, to the substrate. Suitable materials for the film may include hydrophilic materials including polysaccharides such as carrageenan, chondroitin sulfate, glucosamine, pullulan, soluble cellulose derivatives such as hydroxypropyl cellulose and hydroxymethyl cellulose, polyacrylic acid, polyvinyl alcohol, polyethylene glycol (PEG), polyethylene oxide (PEO), ethylene oxide-propylene oxide co-polymer, polyvinylpyrrolidone (PVP), polycaprolactone, polyorthoesters, polyphosphazene, polyvinyl acetate, and polyisobutylene.

The membrane may further be adapted to have a desirable rate of erosion and/or dissolution. The rate may be modified by the inclusion of hydrophobic and/or less soluble additives. Suitable materials may include, but are not limited to, those from the family of quaternary ammonium acrylate/methacrylate co-polymers, (Eudragit RS), cellulose and its lower solubility derivatives, such as butyl cellulose, hydroxybutyl cellulose and ethylhydroxyethyl cellulose, high molecular weight PEG or PEO or a combination thereof.

In yet still other embodiments, the array substrate may be physically divided and/or partitioned for separate collection of the nucleic acids bound to the spots. The spots may, for example, also be controllably removable from the substrate such that they may be individually recovered and sorted. The array itself may also be perforated and/or otherwise easily and/or conveniently partitionable.

In another embodiment, identifiers may be ligated to the bound nucleic acids. For example, a nucleic acid ligase may be utilized to covalently link an identifier sequence to the bound nucleic acid. In general, nucleic acid ligases are enzymes that covalently join two nucleic acids by catalyzing the formation of phosphodiester bonds at the ends of the phosphate backbone of the nucleic acids. Examples of appropriate nucleic acid ligases may include, but are not limited to, E. coli DNA ligase, T4 DNA ligase, T4 RNA ligase, strand break DNA repair enzymes, and/or any other appropriate ligase, modified enzyme, and/or a combination thereof. In general the ligase utilized may be selected based on the form of ligation performed, such as ligation of blunt ends, compatible overhang ("sticky") ends, single stranded DNA, singe stranded RNA and/or any other form of ligation. Further in general, the steps in ligating two nucleic acids together is a one step process that may be carried out at or near room temperature. Further nucleic acid fragments may be utilized to facilitate ligase action, such as appropriate complementary fragments that may aid the formation of a substantially double-stranded nucleic acid complex compatible with a ligase. In general, double stranded ligation may be employed and may utilize substantially compatible overhang fragments to facilitate ligation, or also blunt end ligation may be utilized, such as with either the nucleic acid end or the identifier having a phosphorylated end while the other is unphosphorylated for ligation. Single stranded ligation may also be employed.

Photo ligation may also be employed. Photo ligation may, for example, include covalently linking adjacent nucleic acids by application of electromagnetic energy, such as ultraviolet or visible light. Coupling agents may also be utilized to facilitate the formation of covalent linkages.

In some embodiments, dyes may be included into the identifiers. In one aspect, the identifiers may be doped with dyes. In another aspect, the identifier solutions may be mixed with dyes. According to one embodiment, the dyes may be photosensitive and may be fluorescent. According to another embodiment, the dyes maybe photosensitive and may be phosphorescent.

The substrates used may be glass, ceramic or polymeric, as long as their surfaces promote adhesion between the substrates and the targets. Polymers may include synthetic polymers as well as purified biological polymers. The substrate may also be any film, which may be non-porous or macroporous.

The substrate may be generally planar and may be of any appropriate geometry such as, for example, rectangular, square, circular, elliptical, triangular, other polygonal shape, irregular and/or any other appropriate geometry. The substrate may also be of other forms, such as cylindrical, spherical, irregular and/or any other appropriate form.

Appropriate ceramics may include, for example, hydroxyapatite, alumina, graphite and pyrolytic carbon.

Appropriate synthetic materials may include polymers such as polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymers may be woven or knitted into a mesh to form a matrix or similar structure. Alternatively, the synthetic polymer materials can be molded or cast into appropriate forms.

Biological polymers may be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Any suitable substrate may be susceptible to adhesion, attachment or adsorption by targets. The susceptibility may be inherent or modified. In one example, the surfaces of substrates may be susceptible to adhesion, attachment or adsorption to proteins. In another example, the surfaces of substrates may be susceptible to adhesion, attachment or adsorption to proteins and not to nucleic acids.

In one exemplary embodiment, a glass substrate may have a layer or coating of a material that promotes adhesion with targets, such as proteins, materials that maybe charged, such as those that are positively charged, for binding target materials. Examples of charged materials include cellulosic materials, for example, nitrocellulose, methylcelluose, ethylcellulose, carboxymethyl cellulose, hydroxyethyl cellulose, methylhydroxypropyl cellulose; epoxies, PVDF (polyvinylidene fluoride); partially or fully hydrolyzed poly(vinyl alcohol); poly(vinylpyrrolidone); poly(ethyloxazoline); poly(ethylene oxide)-co-poly(propylene oxide) block copolymers; polyamines; polyacrylamide; hydroxypropylmethacrylate; polysucrose; hyaluronic acid; alginate; chitosan; dextran; gelatin and mixtures and copolymers thereof.

In another exemplary embodiment, if the substrate is not susceptible for attachment by charged materials, or may be susceptible only for attachment by wrongly charged materials, some areas of the substrate may have adhesives, binding agents, or similar attached, adsorbed or coated thereon. Examples of adhesives may include any suitable adhesives that bind the charged materials.

The targets may be present on the substrate discretely or in clusters. The distance between the discrete targets may be close or may be far apart and may usually be of different targets. Clusters may be used for multiple spots of a single target.

In one embodiment, the substrate may be macroporous. Macroporous substrates may be desirable, for example, if the different targets are very close together. When the targets are close by, there may not be sufficient distance between different targets to distinguish which target a biomolecule may be binding to. Closely packed targets may increase the efficiency of the generating of biomolecules. A macroporous substrate may be suited for balancing between efficiency and separation. For a macroporous substrate, the walls of the pores may be sufficient to separate even closely packed targets if the pores are large enough to enable the binding process to occur within the pores.

Also, for macroporous substrates, the pores may have an average diameter greater than the average size of the target material such that the target material may enter or partly enter the pores to anchor. Hydrogels may also be useful for binding or anchoring targets to the pores. Hydrogels may also fill the pores under fluid conditions and present a smooth surface for fluid flow while at the same time may keep the fluid from flowing through the pores.

The plurality of targets may be arranged in any appropriate manner such as, for example, in circular or elliptical spots, square or rectangular spots, stripes, concentric rings and/or any other appropriate arrangement on the subject.

According to one exemplary embodiment, the substrate may be at ambient temperature throughout.

According to another exemplary embodiment, the substrate may include a temperature affecting system that generally produces at least one desired temperature on the surface of the substrate and the adjacent fluid. The desired temperature may facilitate the biomolecule generating process.

According to a further exemplary embodiment, the substrate may include a temperature affecting system for producing a range of desired temperatures on the surface of the substrate and the adjacent fluid. This may be particularly useful when employing a set of targets having a significant range of, for example Tms, or melting temperatures. In one embodiment, the system may include a plurality of temperature affecting devices that are in thermal communication with the substrate. The plurality of devices may generally be disposed such that they may each produce a desired temperature in a given locality on the surface of the substrate. The set of targets may also be distributed on the surface of the substrate such that the temperature at the location of a target is substantially at the Tm of the target.

Temperature affecting devices may be any appropriate device that may substantially produce a desired temperature on a substrate and may include, but are not limited to, thermoelectric devices such as Peltier junction devices, semiconductor heating devices, resistive heating devices, inductive heating devices, heating/cooling pumps, electromagnetic radiation sources and/or any other appropriate devices. Temperature may also be affected by other systems, such as, for example, fluid flows including, but not limited to, water flows, air flows, and/or any other appropriate fluid flows.

In an exemplary embodiment, a plurality of Peltier junction devices may be utilized to generate desired temperatures at localities on the surface of the substrate. Peltier junction devices are particularly useful since they are able to both heat and cool using electrical current. This enables Peltier junction devices to generate temperatures above and below the ambient temperature of a system. They may also be useful in maintaining given temperature conditions at a steady state by adding and removing heat as necessary from the system.

In general, the placement of the temperature affecting devices may determine the temperature profile on the surface of the substrate and the adjacent fluid in the chamber. The temperature affecting devices may thus be disposed at appropriate positions such that given temperatures may be produced and maintained at known positions on the substrate.

The substrate may in general have a given thermal conductivity such that the application of at least one temperature affecting device may substantially generate a temperature gradient profile on the surface of the substrate. In general, the temperature on the surface of the substrate may change as a function of the distance from the position of the at least one temperature affecting device. Substrate materials with a relatively low thermal conductivity may generally produce highly localized temperature variations around a temperature affecting device. Substrate materials with a relatively high thermal conductivity may generally produce more gradual variations in temperature over a given distance from a temperature affecting device. It may be understood that at steady state, the effect of the thermal conductivity of the substrate may not contribute to the temperature profile of the system.

In some embodiments, at least one temperature affecting device may be utilized to produce a particular temperature gradient profile on the surface of the substrate. In general, a temperature gradient may be generated by utilizing at least one temperature affecting device producing a temperature different from the ambient temperature of the system. Multiple temperature affecting devices with at least two producing different temperatures may be utilized to generate a temperature gradient without reliance on the ambient temperature of the system.

The positions and temperatures of multiple temperature affecting devices may be utilized to calculate a resulting temperature gradient profile on the surface of a substrate using standard heat transfer equations. An algorithm may then be utilized to calculate the optimal positions and/or temperatures for a plurality of temperature affecting devices to produce a desired temperature gradient profile on the surface of a substrate. The algorithm may be, for example, applied using a computational assisting system, such as a computer and or other calculatory device. This may be performed to tailor a temperature gradient profile to a particular substrate with a known disposition of targets of known and/or calculated Tm. Similarly, a set of targets of known and/or calculated Tm may be arranged on a substrate based on a temperature gradient profile. This may be desirable as placement of a target at a given location on a substrate may be accomplished more easily than tailoring a temperature profile to pre-existing locations of targets on a substrate. In general, a target may be disposed on the substrate at a temperature address within the temperature profile gradient. The temperature address may, for example, be substantially at the Tm of the target during operation of the molecular hybridization system, and/or any other appropriate temperature.

In another aspect, the molecular hybridization system includes an adjustable system for generating a temperature profile. The adjustable system generally includes a plurality of temperature affecting devices, each affecting the temperature at a particular location of a substrate.

Details of the temperature affecting systems may be found in, for example, U.S. utility patent application Ser. No. 12/249,525, filed on Oct. 10, 2008, entitled "METHODS AND DEVICES FOR MOLECULAR ASSOCIATION AND IMAGING", the contents of all of which are hereby incorporated by reference.

Figure 6:
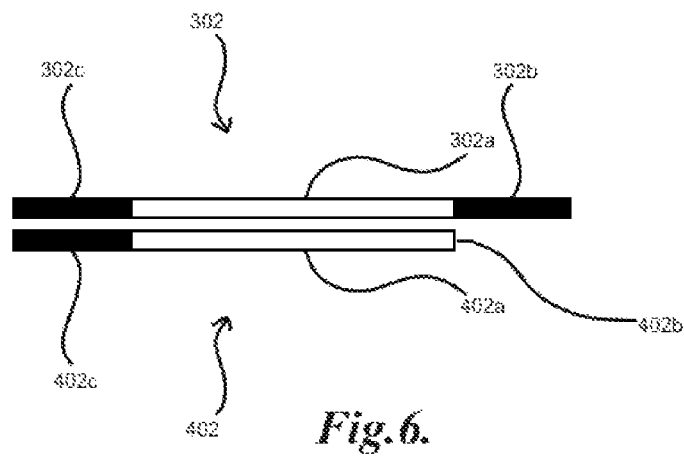
Figure 6A:
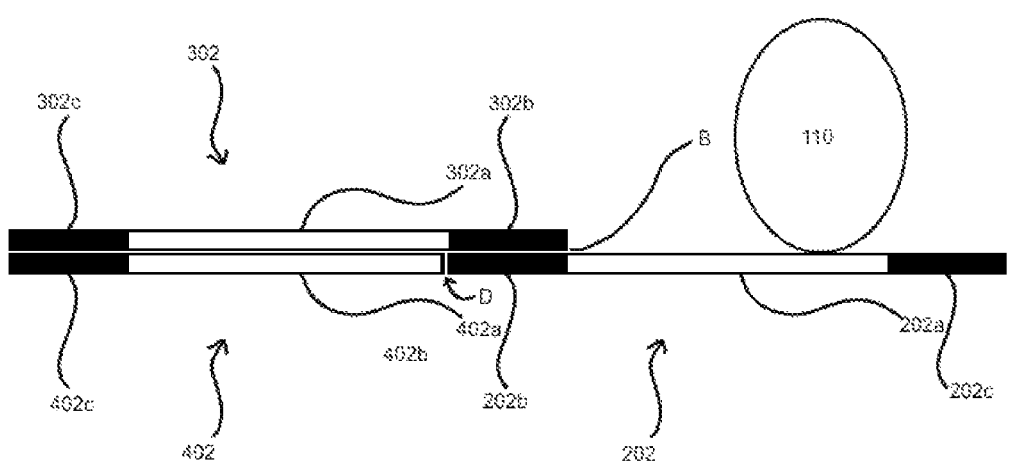
Figure 6B:
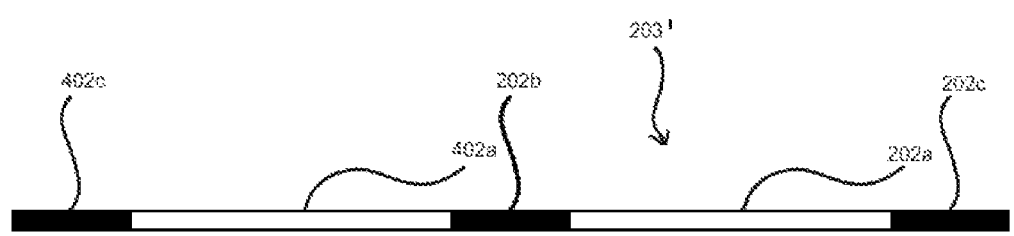

FIG. 6 illustrates an example of an identifier sequence 302 and a complement identifier sequence 402. The complement sequence 402 may include a complement identifier region 402a which may be substantially complementary to identifier region 302a such that they may base pair bind. The complement sequence 402 may further include a primer region 402c which may also be complementary to primer region 302c of the identifier 302. Further, the complement sequence 402 may include a compatible end 402b which may be compatible with ligation to the end of another nucleic acid. As shown in FIG. 6a, a nucleic acid library member 202 may be bound to a spot 110. An identifier 302 and a complement sequence 402 may then be applied to the member 202 such that the identifier 302 binds to the member 202 at region 202b, 302b. The complement sequence 402 may bind to the identifier 302 at regions 302a/402a, 302c/402c. The compatible end 402b may then be ligated to the end D of the member 202 by an appropriate ligase and/or other appropriate method. A product 203', as illustrated in FIG. 6b, may then be generated including the primer region 202c, binding sequence 202a, region 202b, complement identifier region 402a, and complement primer region 402c. The product 203' may then be amplified, such as with the product 203 discussed above in FIG. 4a. The product 203' may also be generated by single-stranded ligation of the member 202 and the complement sequence 402, where in general the either the member 202 or the complement sequence 402 may have a phosphorylated end while the other may be unphosphorylated for end to end ligation.

In another example, as illustrated in FIG. 6c, a further complementary fragment 502 may be included that may base pair bind to a complementary region 202d of the nucleic acid library member 202. This may be desirable as some nucleic acid ligases may generally join double stranded nucleic acids. The addition of the complementary fragment 502 may generally generate a substantially double stranded nucleic acid, such as illustrated spanning from region 302c to the end of complementary fragment 502. There may further be a double stranded "break" at points D and E. In general, the sizing of the fragments may be tailored to generate a suitably long stretch of double stranded nucleic acid for ligase action. In general, the complementary region 202d may be the same for all members 202 of the library 200 such that the same complementary fragment 502 may be utilized, such as, for example, convenience, cost and/or ease of use.

In general, methods may be applied that may facilitate binding or other interactions between the identifiers and the nucleic acids bound to the spots. For example, the temperature may be increased to dissociate the nucleic acids from the spots. The temperature may subsequently be lowered such that, for example, base pairing may occur between the nucleic acids and the identifiers. Temperature changes may also, for example, denature the target such that the nucleic acids may no longer bind and/or bind with lower affinity to the targets. This may be desirable in that it may aid in binding of the nucleic acids to the identifiers.

In a further aspect of the invention, methods for monitoring and/or controlling the diversity of the library of biomolecules may be utilized. For example, too few rounds of selection may result in a biomolecule pool with too many weak binding members while too many rounds of selection may result in only a few binding members, such as members corresponding to only a few targets rather than members corresponding to all of the targets present. In one embodiment, Cot analysis may be employed to measure and/or monitor the diversity of the library of biomolecules through multiple rounds of selection. Cot, or Concentration x time, analysis measures the annealing time of particular oligonucleotides while in solution with other nucleic acids, such as the members of the library of biomolecules. In general, the annealing time will be faster the lower the diversity of the library.

In one embodiment, a Cot-standard curve for measuring the sequence diversity of the aptamer library at any point during the multiplex SELEX process may be utilized. For example, a group of DNA oligonucleotides with a 5'- and 3'-constant region of ~20 bases identical to the initial SELEX library may be utilized. The oligos may then be converted to dsDNA by standard methods. Briefly, after annealing a primer to the oligos, Exo-minus Klenow Taq polymerase (Epicentre, Madison, Wis.) may be used in conjunction with dNTPs to fill in the ssDNA to create a dsDNA or mixture thereof. Using a standard quantitative PCR thermal cycler, a temperature profile for melting and controlled annealing of each DNA mixture may be programmed. Standard SYBR Green I specific for double-stranded DNA (dsDNA) may be utilized to report the amount of re-annealed dsDNA. At one extreme, the annealing time for a single sequence will be measured. At the other extreme, the annealing time for the initial SELEX pool, such as containing approximately 1 nmol of sequence diversity, may be measured. Annealing times of intermediate diversity may also be measured to establish a very specific Cotstandard-curve for the SELEX library. Using this standard curve, at any point during SELEX, the sequence diversity of the evolving library of aptamers may be determined by comparison to the curve.

In a further embodiment, a method for generating functional biomolecules includes obtaining a library of peptide sequences and contacting the library with a plurality of targets. In some embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind another identifier, as described above, such that a peptide bound to a target may be tagged or marked as to which target it bound.

In an exemplary embodiment, a bacteriophage (phage) may be generated that includes a peptide sequence of interest in its protein coat. The phage may further include a nucleic acid sequence that may be representative of the peptide sequence within the nucleic acid of the phage. The phage may then be contacted with a plurality of targets, as above. This may generally be referred to as phage display. Phages employed may include, but are not limited to, M13 phage, fd filamentous phage, T4 phage, T7 phage, λ phage, and/or any other appropriate phage. Non-binding phages may be washed and/or partitioned, while binding phages may be tagged or marked with identifiers, as above. As phage nucleic acids are generally contained within the protein coat of the phage, the nucleic acid may generally be exposed for binding to the identifier. For example, the phage may be heated such that the protein coat denatures and/or disassembles such that the nucleic acid is exposed. The identifier may also be introduced into the phage, such as by electroporation, electrophoresis, and/or any other appropriate method.

In FIG. 7, an example of a phage 600 may include a nucleic acid 610 which may generally encode, among other things, and be encapsulated by a protein coat 602, which may contain a binding region for a target 110. The nucleic acid 610 may further include a region 612 which may identify the phage and/or encode the binding region for a target. A bound phage 600, as illustrated in FIGS. 7 and 7a, may then be heated, disrupted and/or otherwise treated such that an identifier 302 may contact F the region 612. For example, the protein coat 602 may be broken and/or otherwise disrupted for entry of the identifier 302. In general, an amplification reaction and/or other method, such as those discussed above, may be utilized to tag, mark and/or otherwise introduce identifier information to the sequence of region 612. Further in general, the identifier 302 and region 612 may incorporate any, all or a combination of the elements discussed above in regards to nucleic acid library members, identifiers and/or other nucleic acid fragments. As also discussed above, the phage 600 may also be physically removed and/or partitioned in a manner that may preserve the identity of the target 110 the phage 600 was associated.

In other embodiments, other methods of incorporating and/or linking nucleic acids to peptides may be utilized, such as, for example, mRNA display, ribosome display, and/or any other appropriate method. In general, in mRNA display, as illustrated in FIG. 7b, a fusion product 600' of a messenger RNA (mRNA) 610' may be linked to a peptide 602' that the mRNA 610' encodes, such as with a puromycin-ended mRNA 612' which may generally cause fusion of the mRNA 610' to the nascent peptide 602' in a ribosome, which may then be contacted with targets such as described above with phage display. Also in general, in ribosome display, as illustrated in FIG. 7c, a fusion product 600" of a modified mRNA 610" may be utilized that codes for a peptide 602", but lacks a stop codon and may also incorporate a spacer sequence 612" which may occupy the channel of the ribosome 620" during translation and allow the peptide 602" assembled at the ribosome 620" to fold, which may result in the peptide 602" attached to the ribosome 620" and also attached to the mRNA 610". This product 600" may then be contacted with targets such as described above with phage display. Other methods may include, but are not limited to, yeast display, bacterial display, and/or any other appropriate method.

In another aspect of the invention, methods for handling and sorting the resultant sequences of a multiplexed binding process are provided. In some embodiments, the sequences may be sorted by identifier sequences to establish which target or targets the sequence bound. The sequences may further be compared, aligned and/or otherwise processed to identify features, characteristics and/or other useful properties, relationships to each other, and/or target properties. For example, it may be expected that multiple aptamer sequences bound to a single target may potentially share sequence motifs and/or other common features which may be at least partially elucidated by sequence sorting and/or comparison. Specific binding affinities of resultant sequences may also be determined through affinity assays. In some embodiments, surface plasmon resonance may be utilized to determine binding of an aptamer to a target. For example, sensors which monitor the refractive index of a surface bound to a target may be utilized, where the refractive index may change as a result of binding of an aptamer to the target. In general, aside from standard sequencing methods, parallel sequencing methods, such as, for example, massively parallel sequencing such as 454 Clonal Sequencing (Roche, Branford, Conn.), massively parallel clonal array sequencing, Solexa Sequencing (Illumina, San Diego, Calif.), and/or any other appropriate sequencing method may be employed.

Figure 9:
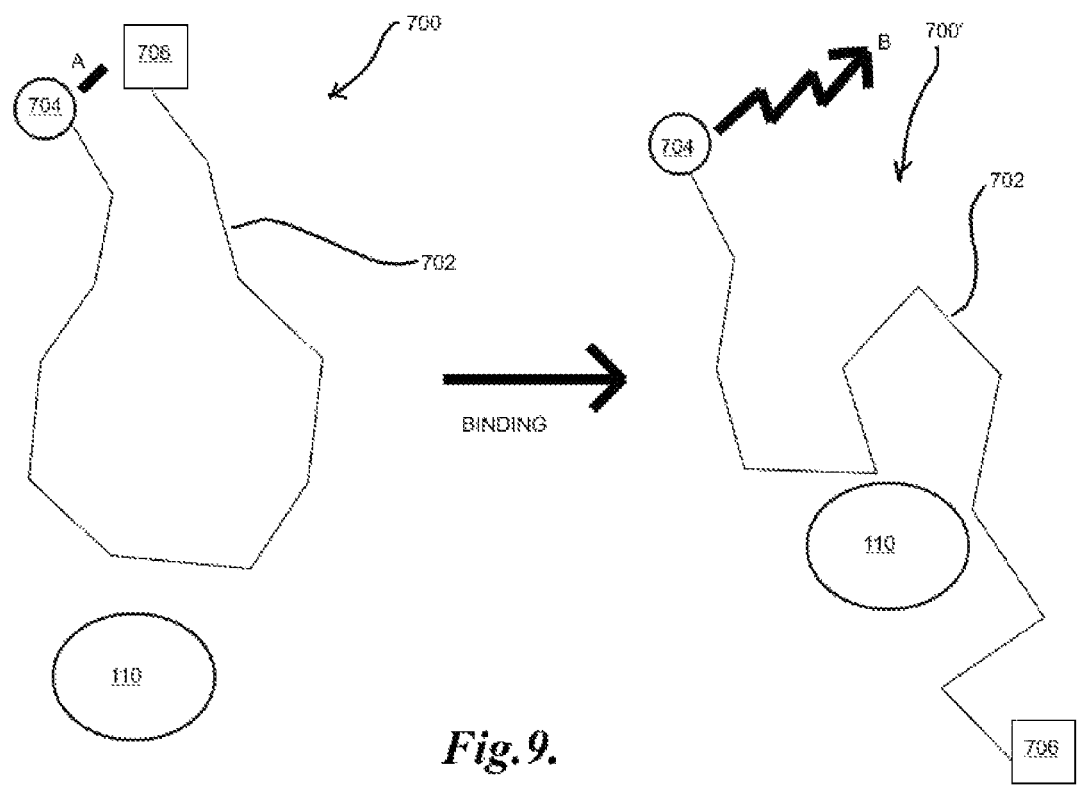
FIG. 9 illustrates an example of binding of an aptabeacon to a target molecule.

Aptamers may also be utilized to create molecular beacons which may fluoresce and/or otherwise produce a detectable signal when the aptamer binds to its target. Aptamers typically undergo a conformational change when binding a target and this conformational change may be utilized to modulate the activity of other molecules or components of a molecule, such as modulating the distance between a fluorophore (fluor) and a quencher. In general, an aptamer beacon or aptabeacon may include an aptamer with a fluor and a quencher attached to the 5' and 3' ends, respectively, or vice versa. The aptamer in its unbound state may generally be designed to keep the fluor and quencher in proximity such that quenching of the fluor occurs and thus little or no fluorescent signal produced. Linkers and/or stem structures may also be utilized with the base aptamer to produce this quenching effect in the unbound state. Such linkers and/or stem structures to produce "beacon" structures in nucleic acids are generally well known and are standard laboratory techniques. When the aptamer binds to its target, its conformational change upon binding may then generally cause spacing of the fluor and quencher such that the fluor may undergo fluorescence without quenching by the quencher, and such fluorescence may then be detected as a signal to indicate binding of the target to the aptamer. FIG. 9 illustrates the conformational changes of an unbound aptabeacon structure 700 when binding to a target molecule 110 at the aptamer portion 702, showing the fluor 704 and quencher 706 in an initial proximity resulting in quenching A and a fluorescence emitting B conformation after binding the target molecule 110 to yield bound conformation 700'.

Aptamers may also be selected and/or designed to exhibit large, detectable and/or specific switching conformational changes when binding to a target molecule. In general, aptamers frequently exhibit induced-fit folding behavior, where the aptamer may be largely unstructured in solution and may undergo significant compaction and/or structural stabilization upon binding its target molecule. In some embodiments, aptamers may be selected and/or designed such that a portion of the aptamer may hybridize to another nucleic acid, such as a primer, anchoring oligo and/or other nucleic acid with a complementary sequence, and may dehybridize from such nucleic acid when the aptamer binds to its target molecule, such as to release the aptamer from such hybridized nucleic acid.

Example of Multiplexed Selex Protocol

As a demonstration of parallel, de novo selection of aptamers against multiple targets, a combinatorial DNA library containing a core randomized sequence of 40 nts flanked by two 20 nt conserved primer binding sites is used as the starting point for an aptamer pool. The primer sequences are designed and optimized using Vector NTI's (Invitrogen) oligo analysis module. Typically, such a library is expected to contain approximately $10^{15}$ unique sequences. The primer binding sites are used to amplify the core sequences during the SELEX process. The single stranded DNA pool dissolved in binding buffer is denatured by heating at 95° C. for 5 min, cooled on ice for 10 min and exposed to multiple protein targets fixed onto a nitrocellulose coated glass slide (e.g., Whatman).

Example Of DNA Library Selex

An example DNA library consists of a random sequence of 40 nucleotides flanked by conserved primers. In the first round of SELEX, 500 pmol of the ssDNA pool is incubated with each slide in binding buffer (PBS with 0.1 mg/ml yeast tRNA and 1 mg/ml BSA) for 30 minutes at 37° C. The slide is then washed in 1 ml of binding buffer for one minute. To elute specifically bound aptamers the slide is heated to 95° C. in binding buffer. The eluted ssDNA is subsequently be precipitated using a high salt solution and ethanol. After precipitation, the aptamer pellet is resuspended in water and amplified by PCR with a 3'-biotin-labeled primer and a 5'-fluorescein (FITC)-labeled primer (20 cycles of 30 sec at 95° C., 30 sec at 52° C., and 30 sec at 72° C., followed by a 10 min extension at 72° C.). The selected FITC-labeled sense ssDNA is separated from the biotinylated antisense ssDNA by streptavidin-coated Sepharose beads (Promega, Madison, Wis.) for use in the next round. Alternatively, "asymmetric PCR" may be utilized for generating a large excess of an intended strand of a PCR product in SELEX procedures. Also alternatively, the undesired strand may be digested by k-exonuclease, such as, for example, when a phosphorylated PCR primer is employed.

The labeling of individual aptamers with fluorescein isothiocyanate (FITC) facilitates the monitoring of the SELEX procedure. FITC is also compatible with scanning in the green (cy3) channel of standard microarray scanners. The sense primer used to amplify the ssDNA aptamers after each round of selection is fluorescently labeled, resulting in fluorescently labeled aptamers. The protein spotted nitrocellulose-coated slides are scanned in a microarray scanner. Alternatively, proteins may be spotted on epoxy-coated glass slides. While epoxy slides may have less protein binding capacity than 3-D nitrocellulose pads, it has been observed that there may be less non-specific binding of nucleic acid aptamer pools to the background of the slide (blocked or not). Blocking may be employed to reduce background fluorescence.

In each round of the SELEX process, the slide is incubated for 30 min at 37° C. to allow binding of the aptamers to their targets. The slides are then washed in binding buffer before the specifically bound DNAs are eluted by heating the slide at 95° C. in 7M urea. Nucleic acids from the eluate are phenol-chloroform purified and precipitated, and the concentrated single stranded DNA molecules will be amplified by PCR. In order to increase stringency throughout the SELEX process, the washes are gradually increased in volume (from approximately 1-10 ml). After a given point in the selection, such as, for example, after the final round of selection, the aptamers may be tagged, marked and/or partitioned.

Example of In Situ Hybridization of Identifiers

An example of in situ hybridization of identifiers to aptamers was performed with short, ssDNA sequence tags to the 3' end of aptamers bound to their protein target. These synthetic ssDNA tag oligonucleotides consists of three regions, as illustrated in FIG. 3b with identifier 302: (i) the C2 region, region 302c of the identifier 302, at the 3' end of the oligonucleotide consists of a 17-20 nucleotide sequence complementary to a corresponding region on all of the used aptamers, (ii) the C1 region, region 302b at the 5' end of the oligonucleotide 302 contains a 17-20 nt primer binding site, used during the amplification of the tag:aptamer hybrid, prior to sequencing and (iii) a variable region 302a in the center of the tag oligonucleotide (V) that serves a as a unique identifier for each locus on the glass slide surface. A variable sequence of 8 nucleotides will allow $4^8$ (65,536) unique sequences to be generated, sufficient for many complex protein arrays (8000 samples) on the market.

As outlined above, after the final round of the SELEX procedure (typically, round 10) the specific aptamers are bound to their protein targets, fixed to a glass slide. While the 40 nt core sequence of each aptamer are unique, its terminal sequences have not been subject to any kind of selection during the procedure. After each round of binding to their protein targets, the aptamers were amplified using conserved primers, requiring the maintenance of corresponding regions at their distal ends (P1, P2). The 3'-region of each aptamer, for instance, can thus serve as a binding site (via standard hybridization) for the C2 region of the proposed tag oligonucleotide. Given the unique variable sequence (V) of each tag oligonucleotide, each aptamer will now be tagged with a sequence that can be traced back to the location of the aptamer on the glass slide, and thus the protein spotted at that location.

Example of Selex Against Targets

A SELEX procedure as described above was performed utilizing target molecules, including LAM, to produce candidate aptamers, and to yield aptamer sequences given in the sequence listing above, with SEQ ID Nos. 1-69 binding to LAM. The sequences yielded are artificial, non-naturally occurring sequences designed and/or selected for artificially for specific and/or high affinity binding to the target molecule and/or similar/related molecules, where the sequences have no known natural function. Any of the sequences, such as SEQ ID Nos. 1-69, may also have SEQ ID Nos. 70 and/or 71 appended to either the 5'-end, 3'-end, or both ends, interchangeably, such as to, for example and without limitation, provide priming sequences, anchoring sequences (e.g. via hybridization), and/or conformational structure switching behavior (e.g. via switching between hybridized to a nucleic acid and unhybridized while bound to a target molecule), yielding aptamers with the general structures: 5'-Seq70-SeqX-Seq71-3', 5'-Seq71-SeqX-Seq70-3', 5'-Seq70-SeqX-3', 5'-Seq71-SeqX-3', 5'-SeqX-Seq71-3' and 5'-SeqX-Seq70-3', where SeqX denotes one of SEQ ID Nos. 1-69.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. An artificial ligand binding to lipoarabinomannan (LAM) comprising a non-naturally occurring nucleic acid sequence under 40 nucleotides in length having substantial homology and greater than 75% identity to a sequence selected from the group consisting of SEQ ID Nos. 5, 7, 8, 14, 19, 23, 34, 54 and 61.

2. The artificial ligand of claim 1 wherein at least one nucleotide is substituted with a non-natural analog.

3. The artificial ligand of claim 1 further comprising an appended 5'-sequence selected from the group consisting of SEQ ID Nos. 70-71.

4. The artificial ligand of claim 1 further comprising an appended 3'-sequence selected from the group consisting of SEQ ID Nos. 70-71.

5. The artificial ligand of claim 1 further comprising an appended 5'-sequence and an appended 3'-sequence selected from the group consisting of SEQ ID Nos. 70-71.

6. An artificial ligand binding to lipoarabinomannan (LAM) comprising a non-naturally occurring nucleic acid sequence having 100% sequence identity to a sequence selected from the group consisting of SEQ ID Nos. 3, 5, 7, 8, 14, 19, 23, 34, 54 and 61.

7. The artificial ligand of claim 6 wherein at least one nucleotide is substituted with a non-natural analog.

8. The artificial ligand of claim 6 wherein said non-naturally occurring nucleic acid sequence is appended with a 5'-sequence selected from the group consisting of SEQ ID Nos. 70-71.

9. The artificial ligand of claim 6 wherein said non-naturally occurring nucleic acid sequence is appended with a 3'-sequence selected from the group consisting of SEQ ID Nos. 70-71.

10. The artificial ligand of claim 6 wherein said non-naturally occurring nucleic acid sequence is appended with a 5'-sequence and a 3'-sequence selected from the group consisting of SEQ ID Nos. 70-71.

* * * * *